(12) United States Patent
Bourne et al.

(10) Patent No.: US 6,476,013 B1
(45) Date of Patent: Nov. 5, 2002

(54) METHOD OF CHLAMYDIA PROPHYLAXIS

(75) Inventors: Nigel Bourne, Cincinnati, OH (US); Lawrence R. Stanberry, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 09/803,295

(22) Filed: Mar. 9, 2001

Related U.S. Application Data

(60) Provisional application No. 60/188,531, filed on Mar. 10, 2000.

(51) Int. Cl.[7] .............................................. A61K 31/33
(52) U.S. Cl. ............................................... 514/185
(58) Field of Search ........................................ 514/185

(56) References Cited

U.S. PATENT DOCUMENTS

| | | | | |
|---|---|---|---|---|
| 5,049,557 A | * | 9/1991 | Dori et al. | 514/185 |
| 5,756,491 A | | 5/1998 | Dori | 514/185 |

* cited by examiner

*Primary Examiner*—Rebecca Cook
(74) *Attorney, Agent, or Firm*—Reed Smith LLP

(57) ABSTRACT

The likelihood of chlamydia infection can be prevented by the topical application of metallo-organic cobalt compounds according to the following formula to the cite of infection:

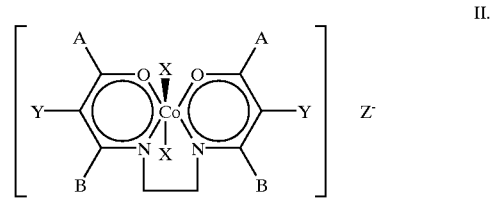

wherein each A may be the same or different and is an alkyl group, a phenyl group or a substituted derivative of a phenyl group; each Y may be the same or different and is hydrogen, an unbranched alkyl group, a halide or a group having the structure wherein R is hydrogen, an alkoxide group, and alkyl group, or OH; each B may be the same or different and each is hydrogen or an alkyl group; each X may be the same or different and each is a water soluble group having weak to intermediate ligand filed strength; and $Z^-$ is a soluble, pharmaceutically acceptable negative ion. Metallo-organic cobalt compounds may also be used to disinfect liquids which contain chlamydia.

19 Claims, No Drawings

METHOD OF CHLAMYDIA PROPHYLAXIS

This application claims benefit of No. 60/188,531 filed Mar. 10, 2000.

BACKGROUND OF THE INVENTION

The present invention relates to metallo-organic cobalt compounds and their use in the prophylactic treatment of subjects to prevent chlamydia infections.

It has been discovered that certain conditions and diseases, e.g., inflammation, burns, wounds, and diseases caused by bacteria, fungi and viruses in mammalian species can be treated with certain complexes of cobalt having the structure:

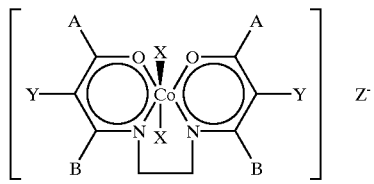

I.

wherein
each A may be the same or different and is an alkyl group, a phenyl group or a substituted derivative of a phenyl group;
wherein each Y may be the same or different and is hydrogen, an unbranched alkyl group, a halide or a group having the structure

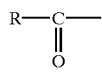

wherein R is hydrogen, an alkoxide group, and alkyl group, or OH;
wherein each B may be the same or different and each is hydrogen or an alkyl group;
wherein each X may be the same or different and each is a water soluble group having weak to intermediate ligand filed strength; and
$Z^-$ is a soluble, pharmaceutically acceptable negative ion.

Today, chlamydia infections are known to be significant causes of morbidity in human and veterinary medicine. Many of these infections present no noticable symptoms, yet can lead to sterility. New prophylactic treatments would decrease the incidence of these infections and improve overall health.

SUMMARY OF THE INVENTION

We have discovered a prophylactic use for the series of compounds having the structure:

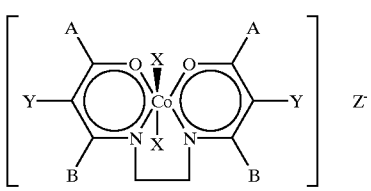

II.

wherein
each A may be the same or different and is an alkyl group, a phenyl group or a substituted derivative of a phenyl group;
each Y may be the same or different and is hydrogen, an unbranched alkyl group, a halide or a group having the structure

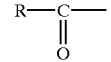

wherein R is hydrogen, an alkoxide group, an alkyl group, or OH;
each B may be the same or different and each is hydrogen or an alkyl group;
$Z^-$ is a soluble, pharmaceutically acceptable negative ion; and
each X may be the same or different and is an axial ligand selected from the group consisting of moieties having the formula:

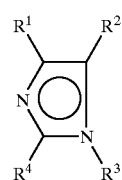

IIa wherein $R^1$, $R^2$, $R^3$, and $R^4$ may be the same or different and maybe hydrogen or lower alkyl having from 1 to 4 carbon atoms; and

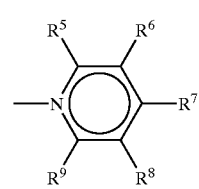

IIb wherein $R^5$, $R^6$, $R^7$, $R^8$ and $R^9$ may be the same or different and may be selected from the group consisting of electron donating groups and electron withdrawing groups;
with the proviso that $R^1$, $R^2$, $R^3$, $R^4$, $R^5$, $R^6$, $R^7$, $R^8$ and $R^9$ are of a sufficiently small size so as not to prohibit the attachment of the axial ligand to the Co atom due to steric hindrance.

As used herein, the term "axial" when used in conjunction with the term "ligand" refers to the fact that the ligand is oriented outside the plane of the molecule and has the same meaning as described in connection with FIG. 1 of U.S. Pat. No. 5,049,557. As used herein, and unless otherwise indicated, an alkyl group means a linear, branched or cyclic alkyl group containing from one to six carbon atoms.

The compounds having the structure of Formula II exhibit prophylactic efficacy when applied as a topical composition to the contact site prior to contact with chlamydia and/or by inactivating chlamydia exposed to the composition. The compositions of the invention may further be used for antisepsis or disinfection of surfaces, such as, surgical tools or preparations such as, media or blood-derived products, which are contaminated with chlamydia.

DETAILED DESCRIPTION OF THE INVENTION

The compounds used in the present invention may be crystallized with numerous counter-anions. Counter-anions which are pharmaceutically acceptable and are water soluble, such as, halide ions, $PF_6^-$ and $BF_4^-$, are preferred. The bromide and chloride salts of the present compounds are the most preferred because they are more water soluble than other salts of the compounds.

As discussed above, A may be an alkyl group, a phenyl group or a substituted derivative of a phenyl group. Preferably, the alkyl group is a $C_1$–$C_5$ group with methyl, ethyl, and butyl groups being particularly preferred. Suitable substituted derivatives of the phenyl group are derivatives wherein each substituent is a halide, an alkyl group or a group having the structure $$R-\underset{\underset{O}{\parallel}}{C}-$$

wherein R is hydrogen, an alkoxide group, an alkyl group or an OH group. To date, the most useful derivatives have proven to be those in which the substituents are halides, or alkyl groups.

Y may be hydrogen, an unbranched alkyl group, a halide or a group having the structure $$R-\underset{\underset{O}{\parallel}}{C}-$$

wherein R is hydrogen, an alkoxide group, an alkyl group or an OH group. In certain embodiments, it is preferred that Y is chlorine, a hydrogen atom or a $C_1$–$C_3$ alkyl group. In embodiments where Y has a structure $$R-\underset{\underset{O}{\parallel}}{C}-,$$

is preferred that R is hydrogen, a methyl group or an OH group.

B may be hydrogen or an alkyl group, and preferably is a $C_1$–$C_3$ alkyl group.

X may be imidazole or pyridinyl groups linked to the cobalt atom through a nitrogen of the ring. The imidazole or pyridinyl nuclei may have hydrogen atoms, or electron donating or withdrawing groups substituted thereon.

The electron withdrawing or donating groups which may constitute appendant groups $R^1$, $R^2$, $R^3$, $R^4$, $R^5$, $R^6$, $R^7$ and $R^8$ are those known in the art to exert the specified electron withdrawing or donating effects on aromatic nuclei. Typical of electron donating groups are $NO_2^-$, $Cl^-$, $Br^-$, and the like. The identity of the particular group is not crucial so long as it does not impart properties to the molecules which are detrimental to the desired properties of the compound, e.g., decreased antiviral activity, increased toxicity, and the like. Additionally, the group must not be so large as to prevent the axial ligand to attach to the cobalt atom due to steric effects, e.g., steric hindrance.

Preferably, the groups attached to the imidazole nucleus are alkyl having from one to three carbon atoms. Of these, methyl and ethyl are most preferred. Preferred are the unsubstituted, 2-methyl, 4-methyl, and 2-ethyl imidazoles and the unsubstituted pyridinyl.

The following Table provides the structures of preferred compounds in accordance with the present invention. Compound 23, which is disclosed in U.S. Pat. No. 5,142,076 as exhibiting antiviral activity, is included as a comparison in the examples that follow.

In the following diagram, B is, in each case, methyl, and A, Y, X and $Z^-$ refer to those symbols as used in structure II.

| COMPOUND | Y | X | Z | A |
|---|---|---|---|---|
| 23 | H | —$NH_3$ | Cl | —$CH_3$ |
| 76 | H | pyridinyl | Br | —$CH_3$ |
| 82 | H | imidazole (H on N) | Cl | $CH_3$ |
| 93 | Cl | imidazole (H on N) | Br | —$CH_3$ |
| 96 | H | 2-methylimidazole | Br | —$CH_3$ |
| 97 | H | 4-methylimidazole | Br | —$CH_3$ |
| 98 | H | imidazole (H on N) | Br | $C_6H_5$ |
| 100 | Cl | 2-methylimidazole | Br | —$CH_3$ |
| 101 | Cl | 4-methylimidazole | Br | —$CH_3$ |
| 102 | H | 2-methylimidazole | Cl | $C_6H_5$ |
| 109 | H | 2-ethylimidazole | Cl | —$CH_3$ |

"Chlamydia" is used herein to mean any one or more of the bacteria in the genus chlamydia. The genus chlamydia includes the species *C. pneumoniae, C. psittaci* and *C. trachomatis.*

The compositions used in the instant invention include a pharmaceutically acceptable carrier and a compound as defined above in a chlamydia prophylactic effective amount. As used herein, the expressions chlamydia prophylactic effective amount, dosage or regimen mean that amount, dosage or regimen which results in a sufficient concentration of the particular compound at an appropriate site to reduce the risk of infection by chlamydia. By appropriate site, it is meant a site which potentially contains chlamydia or is an area of a subject of potential exposure to chlamydia or is an area of a subject that has been exposed to chlamydia but as a result of such exposure, the subject has not yet acquired chlamydia disease. As used herein, the expression acquired chlamydia disease means that the subject, in fact, has the disease and can no longer be treated prophylactically to reduce the risk of infection by chlamydia, but, rather, must be treated therapeutically to cure, ameliorate or reduce the effects of the disease.

For topical administration, the inventive composition may be placed in a pharmaceutically acceptable aqueous solution, ointment, salve, cream or the like. The compounds used in the present invention are water soluble, although the degree of solubility may vary from compound to compound, and may be dissolved in a number of conventional pharmaceutically acceptable carriers. Suitable carriers include polar, protic solvents, such as, water, or normal saline, or non-polar solvents, lipids and the like. The compounds may also be suspended in a suspension medium that is not miscible with water, for example, petrolatum, or may be formulated in an emulsion (water-in-oil or oil-in-water).

When the compounds of formula II are to be administered by the topical route for prevention of infection, i.e., prophylaxis or disinfection, their concentration in an aqueous solution, ointment, salve, creme, or the like can vary from about 0.00005% to about 5% by weight. A preferred concentration range lies between about 0.0005% and about 2% by weight. A particularly preferred concentration range is from about 0.5% to about 2%. Typically, the topical composition shows prophylactic effect when applied to the contact site from about 1 hour before contact with chlamydia to about 6 hours after contact with chlamydia. Preferably, the topical composition is applied within five minutes of contact with chlamydia. More particularly, the inventive compositions can be applied intravaginally for the prevention of sexually transmitted diseases. The topical composition containing the inventive compound could, for example, be applied with an applicator or an intravaginal device or the topical composition could be coated on a condom or other sexual barrier devices.

When the compounds of formula II are to be used for disinfecting liquid preparations, such as, media, blood-derived products or the like, their concentration in the liquid preparations is from about 0.005% to about 5% by weight. A preferred concentration range lies between about 0.05% and about 5% by weight. A most preferred concentration range lies between about 0.01% and about 2% by weight.

General methods for the synthesis of the compounds of the present invention are described in U.S. Pat. No. 5,049,557, referred to and incorporated by reference hereinabove. As noted therein, the reaction of Co(II) complexes with molar oxygen has been studied extensively (see, R. S. Drago and B. R. Corden, Acc. Chem. Res., 1980, 13, 353 & E. C. Niederhoffer, J. H. Timmons and A. E. Martell, Chem. Rev. 1984, 84, 137). Normally, cobalt (II) forms 2:1 peroxo bridged complexes in aqueous solutions (see E. C. Niederhoffer, J. H. Timmons and A. E. Martell, Chem. Rev. 1984, 84, 137). In recent years, a number of Co(II) complexes have been reported to give 1:1 cobalt-oxygen adducts at room temperature. These complexes usually contain ligands which when bound to Co(II) give rise to a low spin planar geometry. Addition of base and $O_2$ to these complexes leads to the formation of octahedral complexes where the base and the $O_2$ occupy axial positions (see, A. Summerville, R. D. Jones, B. M. Hoffman and F. Basolo, J.Chem. Educ., 1979, 56, 3, 157).

On the basis of measurements utilizing a variety of physical techniques, it is now a well-accepted fact that the most accurate electronic structure description of the $Co:O_2$ moiety is a Co(III) ion bound to $O_2^-$ where the actual amount of $Co \rightarrow O_2$ electron transfer depends on the nature of the ligand and the donor set (see, A. Summerville, R. D. Jones, B. M. Hoffman and F. Basolo, J. Chem. Educ. 1979, 56, 3 157, & D. Getz, E. Malmud, B. L. Silver and Z. Dori, J. Am Chem. Soc., 1975, 97, 3846). It has been shown that electron transfer increases with increase of the ligand field strength (see, R. S. Drago and B. R. Corden, Acc. Chem. Res., 1980, 13, 353). This can be easily understood from the molecular orbital diagram depicted in FIG. 1 of U.S. Pat. No. 5,049,557 and the description therein.

The following examples are provided to assist in further understanding the present invention. The particular materials and conditions employed are intended to be further illustrative of the invention and are not limiting upon the reasonable scope thereof.

EXAMPLE 1

Compounds for use with the present invention can be prepared by the following general procedure. In particular, a cobalt-II complex is prepared by mixing equimolar amounts of the N,N'-bisethylenediimine ligands, e.g., L23 and the like as disclosed in U.S. Pat. No. 5,049,557, with cobalt acetate in methanol under nitrogen. About 2.2 equivalents of the desired axial ligand is added followed by oxidation. The desired product may then be precipitated by the addition of a saturated aqueous solution of sodium chloride or sodium bromide followed by recrystallization from an ethanol-water solution.

Compound 96 (having bromide as the counterion) was synthesized as follows:

A 3-neck flask equipped with a nitrogen bubbler and a 2 liter dropping funnel was charged with 112 grams (0.5 moles) of the ligand (L23 or N,N'bis-(acetylacetone) ethylene-diimine) in 500 ml of absolute methanol. To the ligand solution is added 125 grams (0.5 moles) of cobalt acetate tetrahydrate dissolved in 1.5 liters of degassed methanol. The reaction mixture is stirred for 2 hours and then refluxed for 15 minutes on a hot water bath. An orange solution results to which 90 grams (1.1 moles) of 2-methyl imidazole dissolved in 100 ml of methanol are added. The reaction mixture is exposed to the open air while maintaining vigorous stirring. Ten grams of activated charcoal are added to the stirring mixture and the oxidation is continued overnight.

The mixture is then filtered and 50 grams of sodium bromide dissolved in a minimum amount of water is added to the filtered brown solution. The solution obtained is concentrated and allowed to crystallize. The crude product is recrystallized from hot ethanol-water solution by standing at room temperature or a lower temperature. The purity of the product is checked by elemental analysis, electronic spectra and NMR.

EXAMPLE 2

C. trachomatis elementary bodies were incubated for four hours on ice with different concentrations of Compound 96. At the end of that time, serial dilutions were performed on McCoy cell monolayers and the plates were incubated for two days, after which, C. trachomatis titers were enumerated.

When C. trachomatis was incubated with 5 mg/mL Compound 96, no inclusion bodies were detected. When the Compound 96 concentration was reduced to 0.5 mg/mL, there was a 93% reduction in the number of inclusion forming units. At 0.05 and 0.005 mg/mL Compound 96, the inhibitory effect was lost.

EXAMPLE 3

In a study of the mouse model, chlamydia infection was greatly reduced and hydrosalpingitis completely blocked by topical application of Compound 96 prior to challenge with chlamydia. Seventy-eight female Swiss Webster mice were pretreated with medroxyprogesterone acetate and were randomized into three groups to receive either saline (control) (24 mice), 0.5% Compound 96 (27 mice), or 2.0% Compound 96 (27 mice). The animals were anesthetized by intraperitoneal injection of sodium pentabarbital and then the vagina of each animal was swabbed with a moistened calcium alginate tipped swab. The animals were administered 15 $\mu$l of control or test compound intravaginally in one treatment. Twenty seconds later, they were challenged by intravaginal instillation with 15 $\mu$l of a suspension containing 5.0 $\log_{10}$ infection forming units C. trachomatis mouse pneumonitis biovar (MoPn). Vaginal swabs were collected on days 3, 6 and 10 post-challenge to assess the effect of treatment on vaginal replication in the genital tract. In addition, on day 10, approximately half of the animals from each group were sacrificed, the upper genital tract harvested and the magnitude of chlamydia infection determined by quantitative culture. The remaining animals were sacrificed on day 35 post-challenge and the upper genital tract examined for evidence of hydrosalpingitis.

Outcome data for the study is presented in Table 1 below. All of the saline treated control animals developed lower tract infection which spread to the upper genital tract in all animals sacrificed on day 10 post-challenge. Treatment with 0.5% Compound 96 significantly reduced the number of animals which experienced lower genital tract replication but did not impact spread to the upper genital tract. In contrast, treatment with 2% Compound 96 significantly reduced the incidence of isolation of MoPn from both the lower and upper genital tract with the 3 animals that experienced lower tract replication being the only animals in which the organism was isolated from the upper genital tract. Quantitative culture data for Compound 96 treated animals from which the organism was isolated indicated that the titer of MoPn was not significantly reduced. Among animals that were sacrificed on day 35 post-challenge, 50% of controls had hydrosalpingitis in at least one of the oviducts. The incidence was not significantly reduced in animals that received 0.5% Compound 96, but again, 2% Compound 96 proved effective with none of the animals having hydrosalpingitis in either oviduct.

Table 1 below shows the effect of Compound 96 against genital chlamydia infection in a mouse model.

TABLE 1

| Group Having: | Replication in Lower Tract | | Replication in Upper Tract | | Incidence of Hydrosal-pingitis[e] |
| --- | --- | --- | --- | --- | --- |
| | Incidence[a] | D3 Titer[b] | Incidence[c] | Titer[d] | |
| Saline administered | 24/24 | 2.9 ± 0.1 | 12/12 | 2.4 ± 0.1 | 6/12 |
| 0.5% Compound 96 administered | 21/27[f] | 2.8 ± 0.1 | 13/15 | 2.4 ± 0.1 | 5/12 |
| 2.0% Compound 96 administered | 3/27[g] | 3.7 ± 0.1 | 3/16[g] | 2.7 ± 0.1 | 0/11[f] |

[a]Animals from which chlamydia was isolated by culture from vaginal swabs on days 3, 6 or 10 post-challenge/animals innoculated
[b]Mean (±SE) $\log_{10}$ IFU/ml from chlamydia positive animals
[c]Animals from which chlamydia was isolated by culture from upper genital tract homogenates on day 10 post-challenge/animals sacrificed
[d]Mean (±SE) $\log_{10}$ IFU/g from chlamydia positive animals
[e]Animals with hydrosalpingitis/animals sacrificed on day 35 post-challenge
[f]$p < 0.05$
[g]$p < 0.0001$

EXAMPLE 4

In another study of the mouse model, chlamydia infection was also greatly reduced by topical administration of Compound 96 prior to chlamydia challenge. Forty-eight Swiss Webster mice were pretreated with medroxyprogesterone acetate and were randomized into three groups to receive either saline (control) or 2.0% of Compound 96. In particular, sixteen mice received saline (control) twenty seconds prior to chlamydia challenge, sixteen mice received 2.0% Compound 96 five minutes prior to chlamydia challenge, and sixteen mice received 2.0% Compound 96 twenty seconds prior to chlamydia challenge.

The mice were anesthetized by intraperitoneal injection of sodium pentabarbital and then the vagina of each mouse was swabbed with a moistened calcium alginate tipped swab. The mice were then administered 15 $\mu$l of control or test compound intravaginally in one treatment. Either twenty seconds or five minutes later, they were challenged by intravaginal instillation with 15 $\mu$l of a suspension containing 5.0 $\log_{10}$ infection forming units C. trachomatis mouse pneumonitis biovar (MoPn). Vaginal swabs were collected on days 3 and 6 post-challenge to assess the effect of treatment on vaginal replication in the genital tract. In addition, on day 10, the mice were sacrificed and the upper genital tract harvested and cultured to determine whether the mice had experienced ascending infection. The results are shown below in Table 2.

TABLE 2

| Group Having: | Number in group | Number Protected Against in Lower Tract | Number Protected Against in Upper Tract |
| --- | --- | --- | --- |
| Saline administered 5 minutes prior to challenge | 16 | 0 (0%) | 0 (0%) |
| 2% Compound 96 administered 5 minutes prior to challenge | 16 | 5 (31%)[h] | 6 (38%)[h] |

TABLE 2-continued

| Group Having: | Number in group | Number Protected Against in Lower Tract | Number Protected Against in Upper Tract |
|---|---|---|---|
| 2% Compound 96 administered 20 seconds prior to challenge | 16 | 14 (88%)[i] | 14 (88%)[i] |

[h]$p < 0.005$
[i]$p < 0.0001$ vs. saline

As in Example 3, all of the saline treated control mice developed lower and upper tract infection. Treatment with 2% Compound 96 twenty seconds prior to challenge provided good protection of both upper and lower genital tracts. The protection seen when Compound 96 was administrated five minutes before challenge was not as good as Compound 96 administrated twenty seconds prior to challenge. However, treatment with 2% Compound 96 five minutes before challenge significantly reduced the number of mice with lower and upper tract infection.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method for prophylactically reducing the risk of transmission of chlamydia to a recipient and protecting the recipient from infection with chiamydia comprising topically applying a chlamydia prophylactic effective amount to that site on the recipient which is likely to be exposed to chiamydia a composition comprising a chlamydia prophylactic effective amount of a compound having the structure

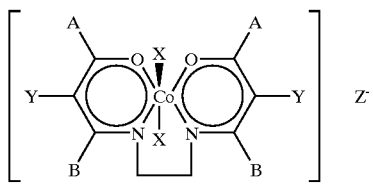

wherein each
A is the same or different and is an alkyl group, a phenyl group or a substituted derivative of a phenyl group;
Y is the same or different and is hydrogen, an unbranched alkyl group, a halide or a group having the structure

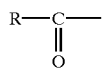

wherein R is hydrogen, an alkoxide group, an alkyl group, or OH;
B is the same or different and each is hydrogen or an alkyl group;
$Z^-$ is a soluble, pharmaceutically acceptable negative ion; and
X is the same or different and is an axial ligand selected from the group consisting of moieties having the formula:

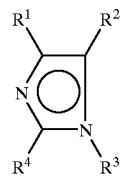

wherein $R^1$, $R^2$, $R^3$ and $R^4$ are the same or different and may be hydrogen or lower alkyl having from 1 to 4 carbon atoms;
with the proviso that $R^1$, $R^2$, $R^3$ and $R^4$ are of a sufficiently small size so as not to prohibit the attachment of the axial ligand to the Co atom due to steric hindrance.

2. The method of claim 1 wherein the compound is from about 0.00005% to about 5% by weight of the composition.

3. The method of claim 1 wherein the compound is from about 0.005% to about 5% by weight of the composition.

4. The method of claim 1 wherein the compound is from about 0.005% to about 2% by weight of the composition.

5. The method of claim 1 wherein the compound is from about 0.5% to about 2% by weight of the composition.

6. The method of claim 1 wherein the composition is in the form of a pharmaceutically acceptable aqueous solution, ointment, salve, creme, or the like.

7. The method of claim 1 wherein the composition is applied intravaginally.

8. The method of claim 1 wherein the composition is applied from about 1 hour before to about 6 hours after exposure to chlamydia.

9. The method of claim 1 wherein the composition is applied from about 5 minutes before to about 5 minutes after exposure to chlamydia.

10. The method of claim 1 wherein the composition is applied from about 20 seconds before to about 20 seconds after exposure to chlamydia.

11. The method of claim 1 wherein the chlamydia is chlamydia trachomatis.

12. The method of claim 1 wherein
A is $CH_3$
Y is H
X is 2-methylimidazole
Z is Br.

13. The method of claim 1 wherein the composition is applied with an applicator or an intravaginal delivery device.

14. The method of claim 13 wherein the applicator is a condom.

15. A method for disinfecting a liquid containing chlamydia comprising adding a composition comprising a chlamydia prophylactic effective amount of a compound having the structure

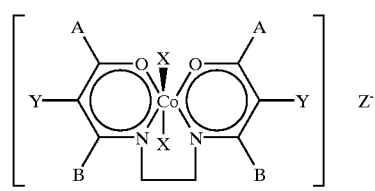

wherein each
A is the same or different and is an alkyl group, a phenyl group or a substituted derivative of a phenyl group;
Y is the same or different and is hydrogen, an unbranched alkyl group, a halide or a group having the structure

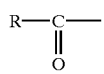

wherein R is hydrogen, an alkoxide group, an alkyl group, or OH;

B is the same or different and each is hydrogen or an alkyl group;

$Z^-$ is a soluble, pharmaceutically acceptable negative ion; and

X is the same or different and is an axial ligand selected from the group consisting of moieties having the formula:

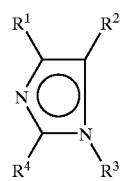

IIa wherein $R^1$, $R^2$, $R^3$ and $R^4$ are the same or different and may be hydrogen or lower alkyl having from 1 to 4 carbon atoms;

with the proviso that $R^1$, $R^2$, $R^3$ and $R^4$ are of a sufficiently small size so as not to prohibit the attachment of the axial ligand to the Co atom due to steric hindrance.

16. The method of claim 15 wherein the compound is added in an amount of about 0.005% to about 5% by weight of the liquid.

17. The method of claim 15 wherein the compound is added in an amount of about 0.05% to about 5% by weight of the liquid.

18. The method of claim 15 wherein the compound is added in an amount of about 0.01% to about 2% by weight of the liquid.

19. The method of claim 15 wherein the liquid is a growth media or a blood-derived product.

* * * * *